United States Patent
Polymeropoulos et al.

(10) Patent No.: US 12,427,132 B2
(45) Date of Patent: Sep. 30, 2025

(54) METHOD OF IMPROVING SLEEP

(71) Applicant: VANDA PHARMACEUTICALS INC., Washington, DC (US)

(72) Inventors: Mihael Polymeropoulos, Potomac, MD (US); Sandra Smieszek, Washington, DC (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 45 days.

(21) Appl. No.: 17/820,025

(22) Filed: Aug. 16, 2022

(65) Prior Publication Data

US 2022/0387374 A1 Dec. 8, 2022

Related U.S. Application Data

(62) Division of application No. 17/429,614, filed as application No. PCT/US2020/018082 on Feb. 13, 2020, now Pat. No. 11,458,116.

(60) Provisional application No. 62/805,057, filed on Feb. 13, 2019.

(51) Int. Cl.
*A61K 31/343* (2006.01)
*C12Q 1/6883* (2018.01)

(52) U.S. Cl.
CPC .......... *A61K 31/343* (2013.01); *C12Q 1/6883* (2013.01); *C12Q 2600/106* (2013.01); *C12Q 2600/156* (2013.01)

(58) Field of Classification Search
CPC ............ C12Q 1/6883; C12Q 2600/106; C12Q 2600/156; A61K 31/343; A61P 25/20
See application file for complete search history.

(56) References Cited

U.S. PATENT DOCUMENTS

2016/0206642 A1 7/2016 Kasajima
2017/0304256 A1 10/2017 Dressman

FOREIGN PATENT DOCUMENTS

WO 2007137244 A1 11/2007

OTHER PUBLICATIONS

Auger et al. (J of Clinical Sleep Medicine, 11, 10, 2015) (Year: 2015).*
Lim et al. (Annals Neurology, 2012, 72, 324-334). (Year: 2012).*
Hida et al. (Scientific Reports, 4 : 6309, p. 1-6). (Year: 2014).*
Patke et al. (Cell, Apr. 6, 2017 169(2), 203-15). (Year: 2017).*
Rajaratnam et al., "The Melatonin Agonist VEC-162 Immediately Phase-Advances the Human Circadian System," Sleep, vol. 29, Abstract Supplement, 2006.
Cardinali et al., "Melatonin and the metabolic syndrome: physiopathologic and therapeutical implications", Neuroendocrinology. vol. 93, 3 (2011): 133-142.
PCT International Search Report and Written Opinion for International Application No. PCT/US2020/018082, dated May 14, 2020, 9 pages.
Bonacci et al., "Tasimelteon (HetloiozTM): A New Melatonin Receptor Agonist for the Treatment of Non-24-Hour Sleep-Wake Disorder," Journal of Pharmacy Practice, vol. 28, No. 5, 22, Oct. 2015.
Polymeropoulos et al., "Tasimelteon for jet lag disorder: results of the JET8 study, a randomized placebo controlled phase 3 trial," Journal of Sleep Research; 24th Congress of the European Sleep Research Society, ESRS 2018, vol. 27, No. Supplement 1, Sep. 1, 2018.
Patke et al., "Mutation of the Human Circadian Clock Gene CRY1 in Familial Delayed Sleep Phase Disorder," Cell 169:203-215 (2017).
Zee et al., "Circadian Rhythm Abnormalities," Continuum 19(1):132-147 (2013).
Wilbur P. (Trey) Williams, III et al. "Comparative Review of Approved Melatonin Agonists for the Treatment of Circadian Rhythm Sleep-Wake Disorders," 2016, Vanda Pharmaceuticals, Inc., 14pages.

* cited by examiner

*Primary Examiner* — Umamaheswari Ramachandran
(74) *Attorney, Agent, or Firm* — Hoffman Warnick LLC

(57) ABSTRACT

The invention provides methods of improving sleep in a patient having a variant of the cryptochrome circadian clock 1 (CRY1) genotype associated with a circadian rhythm sleep disorder (CRSD) Delayed Sleep Wake Phase Disorder (DSWPD).

10 Claims, 2 Drawing Sheets

METHOD OF IMPROVING SLEEP

CROSS-REFERENCE TO RELATED APPLICATIONS

This application is a divisional application of co-pending U.S. patent application Ser. No. 17/429,614, filed 9 Aug. 2021, which is the US national phase of PCT Patent Application Serial No. PCT/US20/18082, filed 13 Feb. 2020, which claims priority to U.S. Provisional Patent Application Ser. No. 62/805,057, filed 13 Feb. 2019, each of which is hereby incorporated herein as though fully set forth.

BACKGROUND

Circadian Rhythm and Sleep

The timing of human sleep is governed by two regulatory processes. The first—the sleep homeostat—preserves the balance between waking hours, during which fatigue accumulates, and sleeping hours, which are restorative and prepare an individual for the next episode of wakefulness. The second—an endogenous rhythm regulated by the circadian pacemaker in the suprachiasmatic nucleus (SCN)—counteracts the effects of fatigue with signals emanating from the circadian pacemaker. In the evening, when the homeostatic drive for sleep is high, wakefulness-promoting signals peak. Then, as an individual approaches bedtime, output from the SCN subsides and sleep ensues.

Sleep-wake disturbances may result from a misalignment of the individual's circadian pacemaker and his/her scheduled sleep time. Such a disturbance is classified as a circadian rhythm sleep disorder (CRSD) and includes various sub-types, including shift work sleep disorder (SWSD), delayed sleep-wake phase disorder (DSWPD), jet lag, and non-24-hour sleep-wake disorder (Non-24).

Several circadian clock genes have been identified. These include the cryptochrome circadian clock 1 (CRY1), cryptochrome circadian clock 2 (CRY2), period 1 (PER1), period 2 (PER2), and period 3 (PER3) genes. Variations in these genes may lead to differences in circadian and sleep/wake cycle phenotypes.

Mutation of the CRY1 gene, for example, has been associated with delayed sleep wake phase disorder (DSWPD), a form of insomnia in which sleep onset and offset are shifted to later times. DSWPD is the most commonly diagnosed type of CRSD, estimated to occur in 0.2%-10% of the general population. Currently, the pathophysiology of DSWPD remains obscure with suspected causes including a differential susceptibility of an individual's circadian clock to environmental entrainment cues such as the light/dark cycle and altered properties of the oscillator affecting its period length. A particular CRY1 allele, rs184039278, has been associated with familial DSPD. This gain-of-function CRY1 variant causes reduced expression of key transcriptional targets and lengthens the period of circadian molecular rhythms, providing a mechanistic link to DSWPD symptoms. In animal studies, expression of this protein resulted in an increase of approximately half an hour in the circadian period.

Melatonin

Melatonin has a distinct circadian pattern. In a healthy nocturnal-sleeping individual, circulating melatonin concentration is low during the waking day, shows a distinct rise about one to three hours before bedtime, remains high throughout sleep, and decreases close to wake-up time. The onset, offset, and midpoint are often used to mark the phase of the endogenous melatonin rhythm. Measurement of circadian phase such as the dim light melatonin onset (DLMO) improves diagnosis and treatment of sleep wake disorders. DLMO may be measured to collect a reliable, non-invasive, circadian phase marker. In DSWPD patients, consistent with a phase delay, entrained DLMO occurs significantly later, well after the time expected in a subject of normal chronotype Tasimelteon Tasimelteon is a circadian regulator that acts as a melatonin receptor agonist with selective activity at Melatonin, Type 1 ($MT_1$) and Type 2 ($MT_2$), receptors. Tasimelteon (HETLIOZ®) has received market authorization for the treatment of the Circadian Rhythm Sleep-Wake Disorder, Non-24, in people over 18 years of age by the Food and Drug Administration and specifically in the totally blind from the European Medicines Agency.

Clinical studies have demonstrated the efficacy of tasimelteon to phase advance the circadian timing system (CTS) and to improve nighttime sleep and decrease daytime sleep, as well as to speed the synchronization of the body clock in totally blind patients with Non-24.

SUMMARY

In a first aspect, the invention provides, in a method of treating patients with a circadian rhythm sleep disorder (CRSD) consisting essentially of administering to said patients an amount of tasimelteon effective to treat said disorder, the improvement comprising: selecting a patient for said treatment by identifying that said patient has a cryptochrome circadian clock 1 (CRY1) genotype associated with said disorder.

In another aspect, the invention provides a method for treating a patient exhibiting one or more symptoms of a circadian rhythm sleep disorder, which comprises: identifying that said patient has a cryptochrome circadian clock 1 (CRY1) genotype associated with said disorder, and administering an amount of tasimelteon to said patient effective to treat said disorder.

In still another aspect, the invention provides a method for improving one or more sleep parameters in an individual, the method comprising: identifying that said individual possesses a variant of the cryptochrome circadian clock 1 (CRY1) genotype associated with a circadian rhythm sleep disorder (CRSD); and administering to said individual daily, at a time proximately before the individual's established bedtime, an amount of tasimelteon effective to improve one or more sleep parameters in said individual.

In yet another aspect, the invention provides, in a method of treating patients with a circadian rhythm sleep disorder (CRSD) consisting essentially of administering to said patients an amount of tasimelteon effective to treat said disorder, the improvement comprising: selecting a patient for said treatment by identifying that said patient has a period 1 (PER1) genotype associated with said disorder.

In another aspect, the invention provides a method for treating a patient exhibiting one or more symptoms of a circadian rhythm sleep disorder, which comprises: identifying that said patient has a period 1 (PER1) genotype associated with said disorder, and administering an amount of tasimelteon to said patient effective to treat said disorder.

In still another aspect, the invention provides a method for improving one or more sleep parameters in an individual, the method comprising: identifying that said individual possesses a variant of the period 1 (PER1) genotype associated with a circadian rhythm sleep disorder (CRSD); and administering to said individual daily, at a time proximately before the individual's established bedtime, an amount of tasimelteon effective to improve one or more sleep parameters in said individual.

DETAILED DESCRIPTION

In a study of genetic variations associated with sleep-wake patterns, Applicant found a significant association between the rs184039278 CRY1 allele and efficacy of treatment with tasimelteon. Specifically, following the administration of tasimelteon before bedtime, individuals having at least one copy of the rs184039278 CRY1 allele exhibited improvements in one or more sleep parameters selected from a group consisting of: latency to persistent sleep (LPS); sleep efficiency (%) during the first, second, and/or final thirds of the night; rapid eye movement (REM) sleep duration; total sleep time (TST), including during the first two-thirds of the night; and wake after persistent sleep (WASO).

Table 1 below shows TST and sleep efficiency data for two individuals diagnosed with DSWPD and having at least one copy of the rs184039278 CRY1 allele who were administered 20 mg of tasimelteon prior to bedtime. As can be seen, these individuals exhibited high TST and sleep efficiency.

TABLE 1

| Group | ID and genotype | Total Sleep Time In First Two-Thirds Of Night (min) | percentage of total sleep time |
|---|---|---|---|
| 20 mg tasimelteon | VP-VEC-162-3107-1 G/T | 308 | 96 |
| 20 mg tasimelteon | VP-VEC-162-3107-2 G/T | 293.5 | 91 |

Figure 1:
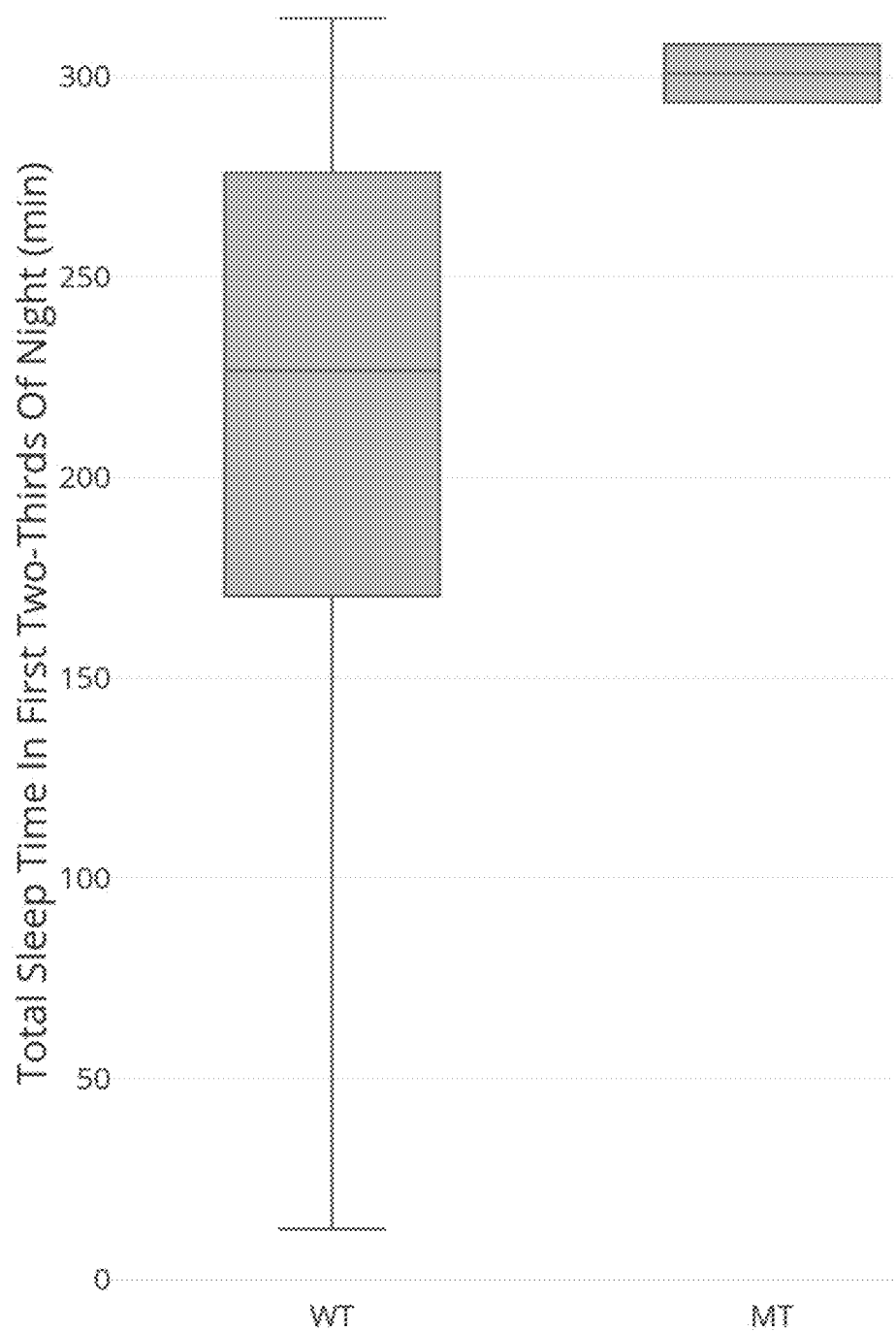
FIG. 1 shows total sleep time (TST) data for two groups of individuals treated with tasimelteon according to the invention—wild type (WT) individuals who do not possess the rs184039278 cryptochrome circadian clock 1 (CRY1) allele and mutant type (MT) individuals who do possess at least one copy of the rs184039278 CRY1 allele.

FIG. 1 shows TST data for individuals having at least one copy of the rs184039278 CRY1 allele (MT) compared to individuals not having at least one copy of the rs184039278 CRY1 allele (WT). Both groups were treated with 20 mg of tasimelteon before bed. As can be seen, TST for WT individuals was both lower and more variable than for MT individuals.

As noted above, the rs184039278 CRY1 allele has been associated with familial DSWPD. What was not known, and not predictable from the literature, was the association between the rs184039278 CRY1 allele and the efficacy of tasimelteon in treating sleep disorders generally or DSWPD specifically.

Other variants of the CRY1 and PER1 genes were also found to be associated with DSWPD. These include the rare rs780614131 allele, which leads to a deletion of exon 6.

For example, Table 2 below shows the observed sleep times of three individuals determined to be heterozygous for the rs780614131 allele. As can be seen, the sleep period of each is delayed as compared to what would be considered a normal or typical sleep period.

TABLE 2

| | Age | Sleep Period |
|---|---|---|
| Individual 1, male | 33 | 2:30 + 30'-11:00 |
| Individual 2, male | 57 | 3:00 + 20'-11:00 |
| Individual 3, female | 28 | 3:30 + 10'-13:00 |

Figure 2:
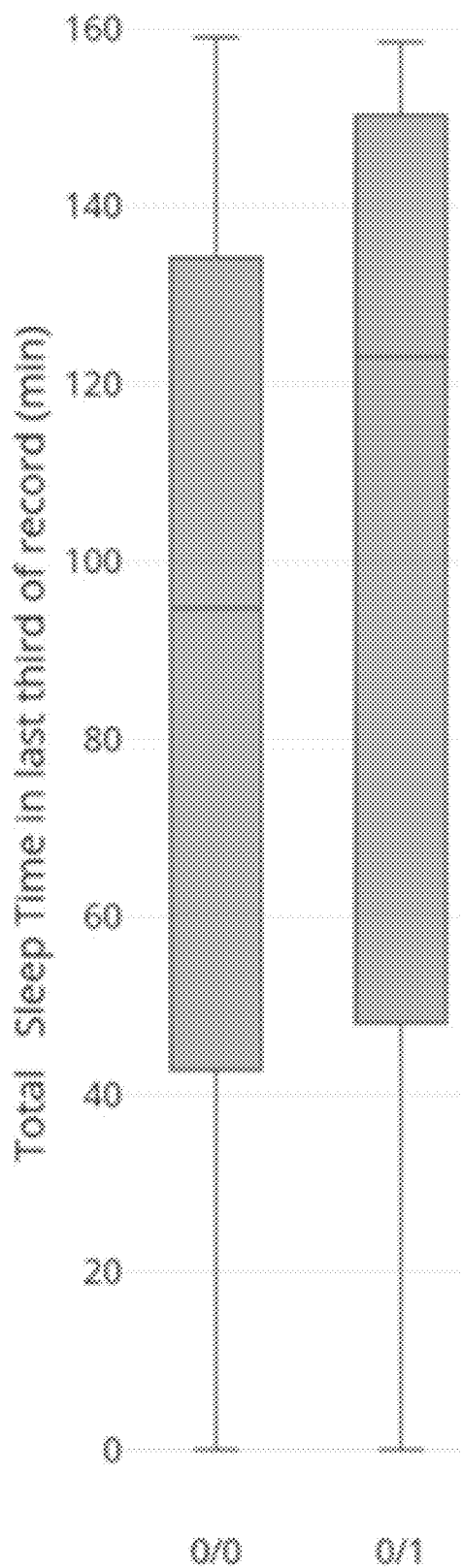
FIG. 2 shows TST during the final third of the night for WT individuals (0/0) who do not possess the rs112474322 PER1 allele and MT individuals who do possess a copy of the rs112474322 allele.

Similarly, individuals heterozygous for the rs112474322 allele exhibited late-shifted sleep during the final third of the night as compared to individuals without the rs112474322 allele. These results are shown in FIG. 2.

Aspects of the invention are applicable to the treatment of any individual having a loss-of-function (LOF) genotype. A LOF genotype is one in which the function of a gene associated with a CRSD (e.g., CRY1 and/or PER1) is reduced or lost, as compared to a wild-type or non-LOF genotype. As one skilled in the art would recognize, a genotype resulting in the complete loss of gene function is a LOF genotype. As one so skilled would also recognize, a genotype resulting in reduced gene function as compared to a wild-type genotype would also constitute a LOF genotype where the reduction in gene function is clinically or phenotypically measurable.

While this invention has been described in conjunction with the specific embodiments outlined above, it is evident that many alternatives, modifications and variations will be apparent to those skilled in the art or are otherwise intended to be embraced. Accordingly, the embodiments of the invention as set forth above are intended to be illustrative, not limiting. Various changes may be made without departing from the spirit and scope of the invention as defined in the following claims. All patents, patent application, scientific articles and other published documents cited herein are hereby incorporated in their entirety for the substance of their disclosures.

What is claimed is:

1. In a method of treating patients with tasimelteon, the improvement comprising:
   selecting a patient for said treatment who has delayed sleep wake phase disorder (DSWPD) and at least one copy of the rs112474322 allele.

2. The improvement of claim 1, wherein treating the patient includes administering tasimelteon to the patient once daily before bedtime.

3. The improvement of claim 2, wherein administering tasimelteon to the patient includes administering 20 mg of tasimelteon.

4. The improvement of claim 1, wherein treating the patient with tasimelteon improves at least one sleep parameter selected from a group consisting of: latency to persistent sleep (LPS); sleep efficiency (%) during the first, second, and/or final thirds of the night; rapid eye movement (REM) sleep duration; total sleep time (TST), including during the first two-thirds of the night; and wake after persistent sleep (WASO).

5. A method for treating a patient exhibiting one or more symptoms of delayed sleep wake phase disorder (DSWPD), which comprises:
   identifying that said patient has at least one copy of the rs112474322 allele; and
   administering an amount of tasimelteon to said patient effective to treat said one or more symptoms.

6. The method of claim 5, wherein the amount of tasimelteon is 20 mg.

7. The method of claim 5, wherein treating said one or more symptoms includes improving at least one sleep parameter selected from a group consisting of: latency to persistent sleep (LPS); sleep efficiency (%) during the first, second, and/or final thirds of the night; rapid eye movement (REM) sleep duration; total sleep time (TST), including during the first two-thirds of the night; and wake after persistent sleep (WASO).

8. A method for improving one or more sleep parameters in an individual suffering from delayed sleep wake phase disorder (DSWPD), the method comprising:
   identifying that said individual has at least one copy of the rs112474322 allele; and
   administering to said individual daily, at a time proximately before the individual's established bedtime, an amount of tasimelteon effective to improve one or more sleep parameters in said individual.

9. The method of claim 8, wherein the amount of tasimelteon is 20 mg.

10. The method of claim 8, wherein the one or more sleep parameters is selected from a group consisting of: latency to persistent sleep (LPS); sleep efficiency (%) during the first, second, and/or final thirds of the night; rapid eye movement (REM) sleep duration; total sleep time (TST), including during the first two-thirds of the night; and wake after persistent sleep (WASO).

* * * * *